United States Patent [19]

Angers et al.

[11] 4,311,686

[45] Jan. 19, 1982

[54] METHODOLOGY FOR THE IMMUNODIAGNOSIS OF MULTIPLE SCLEROSIS AND/OR MALIGNANT DISEASES FROM BLOOD SAMPLE ANALYSIS

[75] Inventors: John W. Angers, Red Bank, N.J.; Lazar Korik, Brooklyn, N.Y.

[73] Assignee: The Immunology Development Corporation, Red Bank, N.J.

[21] Appl. No.: 87,024

[22] Filed: Apr. 30, 1979

[51] Int. Cl.$^3$ .................... G01N 33/54; G01N 33/56; C07G 7/00
[52] U.S. Cl. ..................... 424/1; 23/230 B; 260/112 B; 424/12; 435/3
[58] Field of Search .................... 424/1, 12; 23/230 B; 435/3; 260/112 R, 112 B

[56] References Cited

U.S. PATENT DOCUMENTS 4,136,160 1/1979 Cohen ....................................... 424/1
4,146,603 3/1979 Davidson et al. ....................... 424/1

OTHER PUBLICATIONS

Fruitstone et al., WO 79/00796, Oct. 18, 1979.

*Primary Examiner*—Christine M. Nucker
*Attorney, Agent, or Firm*—Lee C. Robinson, Jr.

[57] ABSTRACT

New and improved methodology for the diagnosis of a disease from blood sample analysis is disclosed and comprises: the preparation of a putative antigenic body substance extract, which is specific to disease-sensitized blood leukocytes, from the pooled, like body substances of a plurality of donors known to have the disease of interest; the mixture of said extract with the blood sample leukocytes; the promotion of the reaction therebetween to modify a characteristic of the disease-sensitized leukocytes, if any, of the blood sample; and the determination of the extent, if any, to which said characteristic has been modified. In multiple sclerosis diagnosis, said body substance may be blood or urine; while for malignant disease (for example breast cancer, or cancer of the head and neck) said body substance may be blood, urine, pleural fluid, ascites fluid, supernates of tumor cells or tumor cells grown in culture media.

50 Claims, 4 Drawing Figures

FIG. 1

DISTRIBUTION OF NON-ADHERENCE INDEX (NAI) VALUES IN NORMAL PATIENTS, NORMAL CONTROLS, AND NON-MS DISEASE CONTROLS.

NON-ADHERENCE INDEX VALUES FOR
MS PATIENTS AND CONTROL SUBJECTS

|  | MULTIPLE SCLEROSIS | CONTROLS |
|---|---|---|
| NUMBER | 58 | 75 |
| POSITIVE | 53 | 3 |
| PERCENTAGE | 91.4% | 4% |
| RANGE | 106.2 TO -2.9 | 31 TO -43.9 |
| MEAN NAI | 42.4 | -2.89 |
| STANDARD DEVIATION | 20.93 | 14.9 |

FIG. 2

NAI VALUES OF 10 MS PATIENTS -
LAI REPEATED AT INTERVALS

|  | 1 | 2 | 3 | 4 |
|---|---|---|---|---|
| MS 1 | 56 | 49 | 48 |  |
| MS 2 | 32 | 60 | 27 | 31 |
| MS 3 | 72 | 38 |  |  |
| MS 4 | 41 | 61 | 44 |  |
| MS 5 | 41 | 23 |  |  |
| MS 6 | 34 | 24 |  |  |
| MS 7 | 32 | 49 | 40 |  |
| MS 8 | 33 | 47 | 43 | 34 |
| MS 9 | 54 | 32 |  |  |
| MS 10 | 76 | 66 | 47 | 71 |

FIG.3

MEAN NON-ADHERENCE INDEXES AS DETERMINED BY LEUKOCYTE ADHERENCE INHIBITION ASSAY IN THE PRESENCE OF VARIOUS PUTATIVE ANTIGENIC EXTRACTS. NAI OF >20 CONSIDERED POSITIVE.

| DISEASE OF LEUKOCYTE (BLOOD SAMPLE) DONOR | PUTATIVE ANTIGENIC EXTRACTS | | | | | | | |
|---|---|---|---|---|---|---|---|---|
| | HEAD AND NECK CANCER | | MULTIPLE SCLEROSIS | | BREAST CANCER | | | |
| | MEAN NAI | NUMBER TESTED | MEAN NAI | NUMBER TESTED | MEAN NAI | NUMBER TESTED | MEAN NAI | NUMBER TESTED |
| HEAD AND NECK CANCER | 34.4 | 38 | -0.2 | 20 | 2.5 | 25 | | |
| MULTIPLE SCLEROSIS | -9.0 | 10 | 40.5 | 46 | 1.6 | 36 | | |
| BREAST CANCER | -1.6 | 23 | 2.9 | 42 | 41.6 | 37 | | |
| CONTROLS (NORMAL OR DISEASES OTHER THAN SPECIFIED) | -1.6 | 59 | 1.9 | 74 | 0.3 | 99 | | |

FIG. 4

METHODOLOGY FOR THE IMMUNODIAGNOSIS OF MULTIPLE SCLEROSIS AND/OR MALIGNANT DISEASES FROM BLOOD SAMPLE ANALYSIS

BACKGROUND OF THE INVENTION

1. Field of the Invention

This invention relates to new and improved methodology for the immunodiagnosis of multiple sclerosis and/or malignant diseases from blood sample analysis.

2. Description of the Prior Art

Although a variety of techniques are, of course, known for the diagnosis of multiple sclerosis, such techniques will generally be found to be costly and time consuming in requiring relatively lengthy, precise and painstaking patient examination by particularly highly trained neurological specialists in order to arrive at presumably definitive diagnostic results. Furthermore, since multiple sclerosis does not manifest itself in the form of a tumor or like diseased tissue in the body, with the possible exception of change in certain sections of the brain, it will be readily understood by those skilled in this art that traditional malignant disease diagnostic techniques in the nature, for example, of tissue and/or cell biopsy, are totally inapplicable to the diagnosis of multiple sclerosis, it having, in any event, proven impossible to date as a practical matter to identify and extract diseased tissue from a live brain for diagnostic study. In addition, and although there are, of course, a wide variety of diverse techniques available for the positive diagnosis of malignant diseases in the nature, for example, of breast cancer, and cancer of the head and neck, which are manifested in the form of diseased tissue, the diagnostic techniques will generally be found to ultimately require surgical removal and analysis of live diseased tissue and/or cell samples, with attendant patient discomfort and need for relatively lengthy, precise and painstaking administration by particularly highly trained medical specialists, to fully validate the results thereof. All of the above is to say that there is not currently known and in use any truly reliable, positive diagnostic technique which requires only blood sample analysis for the valid, specific and clinically reproducible diagnosis of multiple sclerosis and/or malignant diseases.

OBJECTS OF THE INVENTION

It is, accordingly, an object of our invention to provide new and improved methodology for the immunodiagnosis of multiple sclerosis and/or malignant diseases from blood sample analysis.

Another object of our invention is the provision of methodology as above which provides highly accurate, specific and readily reproducible positive diagnostic results.

Another object of our invention is the provision of methodology as above which, in large measure, consists of relatively uncomplicated steps to thus enable the effective and reliable administration thereof by appropriately trained laboratory technicians as opposed to highly trained medical specialists.

Another object of our invention is the provision of methodology as above which is effective to materially reduce the patient discomfort, time required, and overall cost attendant positive diagnosis of multiple sclerosis and/or malignant diseases.

Another object of our invention is the provision of methodology as above which is, in not insubstantial measure, particularly adaptable to automation, to even further reduce the time and cost requirements thereof.

Another object of our invention is the provision of methodology as above which advantageously enables the preparation of putative antigenic multiple sclerosis-specific test extracts and non-specific control extracts, from the pooled bloods or urines of donors known to have multiple sclerosis, and the preparation of putative antigenic cancer type-specific test extracts, and non-specific control extracts, from the pooled bloods, urines, pleural fluids, ascites fluids, supernates of tumor cells, or tumor cells grown in culture media, respectively, from donors known to have the specific type of cancer of interest, and those known not to.

Another object of our invention is the provision of methodology as above which advantageously enables the quantity preparation, well in advance of actual diagnostic testing of patients, of putative antigenic, disease-specific test extracts, and non-specific control extracts which may readily be frozen for effective, long-term storage and/or shipment thereof.

A further object of our invention is the provision of methodology as above which advantageously enables the determination of diagnostic test results through use of a variety of different procedures.

SUMMARY OF THE DISCLOSURE

As disclosed herein, the new and improved methodology of our invention is based upon the discovery that a multiple sclerosis related material is present in and may be extracted from the pooled whole bloods of donors known to have multiple sclerosis in accordance with currently accepted diagnostic techniques; and that this material has putative, specific antigenic characteristics when appropriately reacted with the disease-sensitized leukocytes (white blood cells) of a whole blood sample from a patient with multiple sclerosis. More particularly, these putative antigenic characteristics of the extracted material effect a specific decrease in the ability of the disease-sensitized leukocytes of the multiple sclerosis patient blood sample, probably as a result of altered cell-mediated immunity, to adhere to a glass surface, thus making possible the prompt and reliable determination of the extent of the putative antigenic extract-sensitized leukocyte reaction by leukocyte adherence inhibition or related assay. Control extracts for assay purposes are prepared from the pooled bloods of donors known not to have multiple sclerosis. This discovery has been extended in like manner to the preparation of putative antigenic extracts from the pooled whole bloods of donors known to be suffering from malignant diseases in the nature, for example, of breast cancer, and cancer of the head and neck; and the appropriate reaction of these putative antigenic extracts with the disease-sensitized leukocytes of a whole blood sample from a patient having the like disease. Again, control extracts are prepared as above and leukocyte adherence inhibition assay or related test procedure is utilized to determine the extent of the putative antigenic extract-sensitized leukocyte reaction. A minimum, leukocyte non-adherence or related index value has been determined as positively indicative of multiple sclerosis or the malignant disease in question in each instance. Thus, for example, a non-adherence index value of greater than 20 attendant utilization of the new and improved methodology of our invention by way of leukocyte adherence inhibition assay is deemed to warrant a positive diagnosis of multiple sclerosis. Of particular significance with regard to the above are the specificity and clinical reproducibility of the antigenic extract-sensitized leukocyte reaction. This is to say, for example, that the putative antigenic extract as prepared from the blood of a donor known to have multiple sclerosis will not appreciably react with, or affect the ability of, the leukocytes from a healthy patient, or the disease-sensitized leukocytes from one suffering, for example, from breast cancer, to adhere to a glass surface. In addition, the clinical reproducibility of the test procedures render the same particularly adaptable for widespread diagnostic application, especially since the various putative antigenic extracts can be prepared well in advance of actual utilization and stored for long periods by freezing; while the relatively uncomplicated nature of the test procedures render the same readily and effectively administrable by appropriately trained medical technicians. In addition, the nature of the test procedures is such that they are readily adaptable to automation. Alternative preparation of the putative antigenic extract for multiple sclerosis diagnosis from the pooled urines of donors known to have multiple sclerosis, and alternative preparation of the putative antigenic extract for cancer diagnosis from the pooled urines, pleural fluids, ascites fluids, supernates of tumor cells, or tumor cells grown in culture media, respectively, of patients known to have the specific type of cancer of interest, are also disclosed in accordance with the teachings of our invention.

DESCRIPTION OF THE DRAWINGS

The above and other objects and significant advantages of our invention are believed made clear by the following detailed description thereof taken in conjunction with the accompanying drawings wherein.

DETAILED DESCRIPTION OF THE INVENTION

Utilization of the new and improved methodology of our invention for the positive, immunodiagnosis of multiple sclerosis (hereinafter "MS"), or a specific malignant diseases of interest in the nature, for example, of breast cancer, or cancer of the head and neck, from blood sample analysis is typically effected attendant the following steps; it being understood that the nature and purpose of these steps may vary somewhat in accordance with the requirements of the specific test procedure to be utilized, all as described in detail hereinbelow:

(a) Preparation of a whole blood sample from a patient in question to isolate the blood sample leukocytes (white blood cells);

(b) Preparation of a putative antigenic, specific MS related material, or specific malignant disease of interest related material (hereinafter the "test extract") from the pooled bloods of donors known to have MS or the specific malignant disease of interest, and preparation of the control extract from the pooled bloods of donors known not to have MS or the specific malignant disease of interest;

(c) Preparation of a test sample by mixture and reaction of a portion of the prepared blood sample of (a) with the test extract of (b) with resultant inhibition of the ability of the sensitized blood sample leukocytes to adhere to a glass surface in specific accordance with the quantitative extent of the reaction; and preparation of a control sample by mixture and reaction, if any, of another portion of the blood sample of (a) with the control extract of (b); and (d) Determination by test and control sample assay of the non-adherence index (hereinafter "NAI") or related characteristic of the thusly reacted leukocytes of the test sample of (a) to thus detect MS or the specific malignant disease of interest on the part of the patient in question.

Advantageously, clinical utilization of these steps for the positive diagnosis of MS, or specific malignant disease of interest, in a patient may be accomplished in accordance with the teachings of our invention through use of any one of a number of test procedures including: (1) a leukocyte adherence inhibition procedure; (2) a latex or microsphere procedure; (3) a radio immunoassay or micro leukocyte adherence inhibition procedure; and (4) a lysis procedure, all as more specifically described hereinbelow; it being readily understood by those skilled in this art that sterile techniques would be used throughout each of these procedures, and that all times, temperatures, quantities, concentrations, g-loading factors, pressures, structural configurations and like specifications, are representative, only, of those which have proven effective for the purposes disclosed, with regard to the procedure of interest, and that the same may vary within the scope of our invention as limited only by the relevant recitations of the appended claims.

(1) Positive diagnosis of MS through use of leukocyte adherence inhibition procedure is accomplished in accordance with the teachings of our invention as follows:

Blood Sample Preparation:

Twenty-five ml of venous blood, preferably heparinized at 250 units/ml, is withdrawn from the patient in question into a 30 ml plastic syringe, and the latter inverted and stored for 1 hour at 25° C. to provide for initial blood sample separation, whereupon the blood sample is incubated at 37° C. for ½ hour. The leukocyte-rich plasma is then drawn off and centrifuged at 200×g for 5 minutes at 25° C., whereupon the resultant supernate is discarded and the now predominantly white cell pellet resuspended in 2.5 ml of 0.8% ammonium chloride (adjusted, for example, with 1 N NaOH to pH 7.2) and allowed to stand for 15 minutes at 4° C. to lyse the remaining red blood cells. The cell pellet is then washed three times in 5 ml of Medium 199 (Gibco preparation containing 25 mm Hepes Buffer Glutamine and Hanks Balanced Salts), and the final suspension adjusted with additional Medium 199 as required, through use, for example, of a Coulter or like white cell counter, to a concentration of $1 \times 10^7$ leukocytes per ml.

Test And Control Extract Preparation:

Twenty ml of venous blood is withdrawn into plastic syringes from each of a group of at least 5 donors, all known to have clinically definite MS in either the relapsing or progressive phase of the disease in accordance, for example with the Rose et al. diagnostic criteria as described in the article entitled "Criteria For The Clinical Diagnosis of Multiple Sclerosis" by A. S. Rose, et al. from *Neurology* 26/6:20, 1976. This MS patient blood is pooled and, if not for immediate use, is readily storable at −20° C. For use in test extract preparation, following thawing if required, the MS blood is mixed with 5 volumes of 3 M KCl. and the resultant solution stirred automatically for 16–24 hours at 4° C. to insure the thorough mixture thereof, whereupon the solution is centrifuged at 40,000×g for one hour at 4° C. The resultant supernate is dialyzed for 12–16 hours in a 26 mm cellophane membrane, with a molecular weight cut-off in the range of 12,000 to 14,000 daltons, against two liters of phosphate buffered saline of pH 7.4 with three changes of buffer. The resultant non-dialysate is centrifuged at 40,000×g for 15 minutes at 4° C. and the resultant supernate concentrated to 30 ml in a sterile 90 mm Millipore Ultra Filtration Unit with a PSAC membrane, with purified nitrogen at 40 psi being used to propel the solution through the membrane. The resultant retentate, which is never allowed to dry, is diluted with PBS to 50 ml, and clarified by centrifugation at 40,000×g for 15 minutes at 4° C. to complete the preparation of the specific or test extract. Storage of the extract is preferably effected in 1 ml aliquots at −60° C. Preparation and storage of the non-specific or control extract is effected in the same manner as preparation and storage of the test extract but from the pooled bloods of each of a group of at least five donors known not to have MS.

Test And Control Sample Preparation:

The respective test and control extracts are thawed, if necessary, and diluted to protein concentrations of approximately 5 mg/ml (1:30 dilution) with Medium 199. 0.1 ml aliquots of the thusly diluted test and control extracts are then respectively dispensed into disposable glass tubes (for example, Tek Disposable, 16×150 mm as marketed by Abbott Laboratories, South Pasadena, Calif.) which have been thoroughly pre-cleaned with ethyl alcohol. 0.1 ml aliquots of the prepared blood sample and 0.3 ml of Medium 199 are added to each of the disposable glass tubes and the resultant mixtures incubated, with the tubes horizontally positioned, at 37° C. for two hours to thus complete the preparation of the respective test and control samples.

Test And Control Sample Assay:

MS detection on the part of the patient in question is effected through use of the basic leukocyte adherence inhibition (hereinafter "LAI") assay, as described in the article entitled "Leukocyte Adherence Inhibition; A Simple Test For Cell-Mediated Tumor Immunity And Serum Blocking Factors" by W. J. Halliday, et al. from *International Journal of Cancer* 39:449, 1977; as modified in part in the manner described in the article entitled "Capillary Tube Leukocyte Adherence Inhibition: An Assay For Cell-Mediated Immunity In Cancer Patients" by M. M. Urist, et al. from *International Journal of Cancer* 17:388, 1976, and as refined in accordance with the teachings of our invention; it being readily understood by those skilled in this art that the LAI assay functions to measure the ability of the leukocytes of the respective test and control samples to adhere to a glass surface by counting those of the same which do not so adhere. Prior to assay, a procedure control sample consisting of 0.1 ml of patient's blood sample, prepared as above, and 0.4 ml of Medium 199 is pipetted into a plastic cuvette containing 20 ml of Isoton or like cell-counting solution, and a Coulter Electronic Cell Counter, of the type manufactured and marketed by Coulter Electronics, Inc. of Hialeah, Florida, or like device, is utilized to count the leukocytes (white blood cells); it being understood that a count of less than 5,000 or greater than 15,000 cells per cc is indicative of either an abnormally low or high white cell count on the part of the patient of interest, or error in blood sample preparation or white cell counting. In such instance, correction in blood sample preparation or cell counting technique, or change in blood sample concentration, will be required before assay can proceed. Test and control extract background cell counts are then obtained with, in each instance, 0.1 ml of the relevant extract being mixed with 0.4 ml of Medium 199 and Isoton, and electronic cell counting accomplished as above. For Assay, 0.1 ml aliquots of the respective test and control sample suspensions are pipetted into plastic cuvettes each containing 20 ml of Isoton II or like cell-counting solution, Counter and the cell counter then utilized to count the non-adherent leukocytes (white blood cells) from each of the test and control sample suspensions, it being understood that all assays are preferably conducted in triplicate with attendant mean calculation. The assay results are expressed in terms of the NAI in accordance with the following equation:

$$NAI = 100 \times (A-B)/B \qquad \text{Equation 1}$$

wherein:

A is the mean number of non-adherent leukocytes in the presence of specific antigens minus the test extract background count, and B is the mean number of non-adherent leukocytes from the control sample minus the control extract background count.

Figure 1:
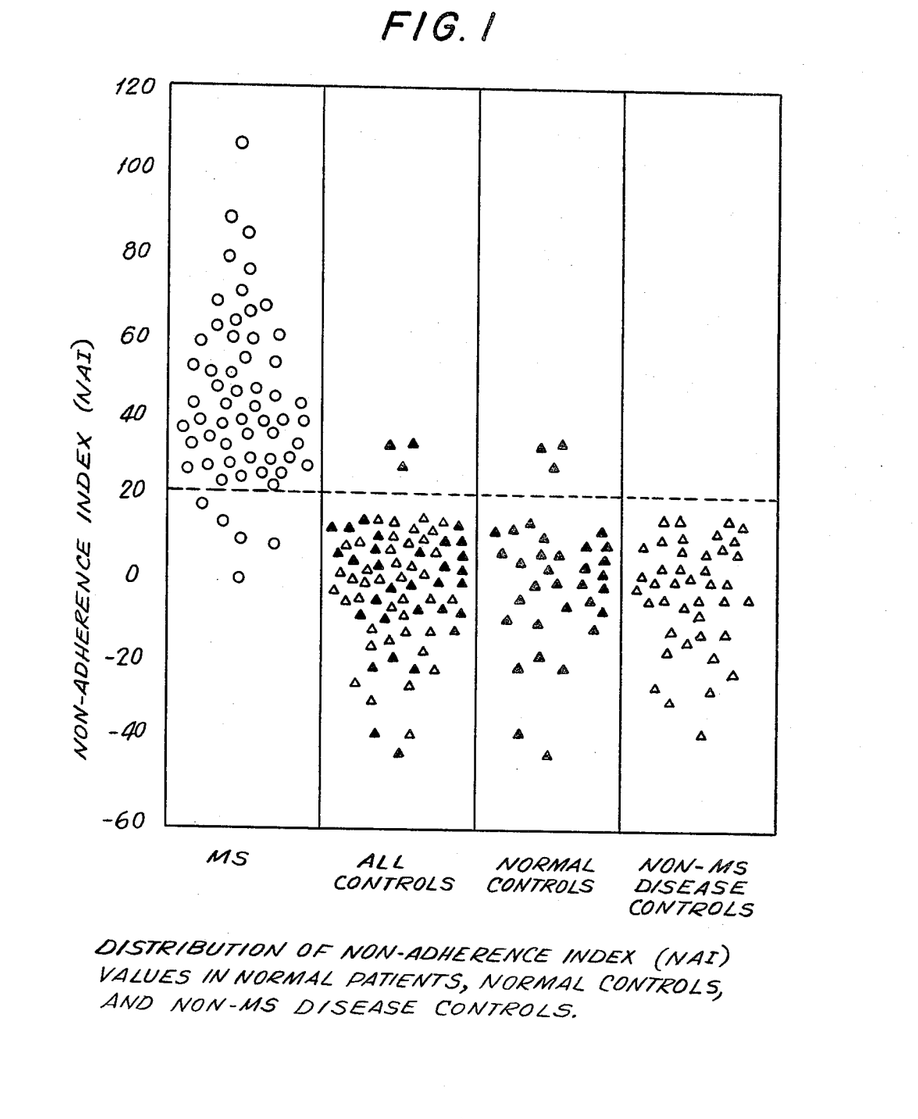
FIG. 1 is a scattergram illustrating the results provided by a typical application of the new and improved methodology of our invention.

Validation of the new and improved methodology of our invention is believed provided by the results of a test program conducted on respective test and control groups, with the former being constituted by 58 patients known to have clinically definite MS in accordance with the Rose, et al. diagnostic criteria as discussed hereinabove, and the latter being constituted by 75 subjects consisting of 34 normal subjects, and 41 subjects known to have a variety of medical and neurological diseases other than MS. The results of this test program are depicted in scattergram form in FIG. 1, it being noted that an NAI value of greater than 20 has been selected as positive indicia of patient MS on the basis of the distribution of the thusly obtained NAI values. As depicted in FIG. 1, fifty-three of the 58 (91.4%) MS patients of the test group were positively identified by the NAI assay as having MS, while seventy-two of the 75 (96.0%) subjects of the control group were positively identified as not having clinical MS. Technical error in the testing procedures is believed responsible for the NAI values below 20 attributable to five MS patients of the test group, and for the NAI values above 20 attributable to three non-MS subjects of the control group.

Figure 2:
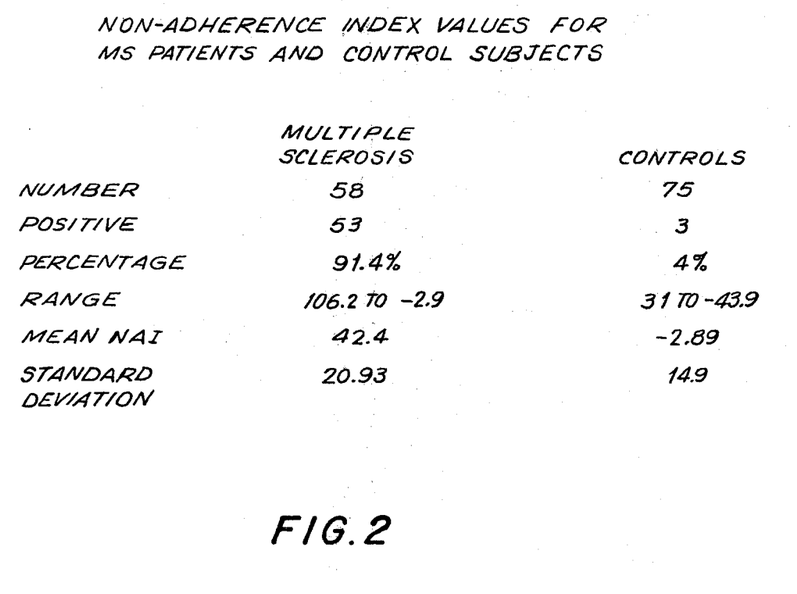
FIG. 2 is a table setting forth typical non-adherence index values obtained through an application of the methodology of our invention to the diagnosis of multiple sclerosis.
Figure 3:
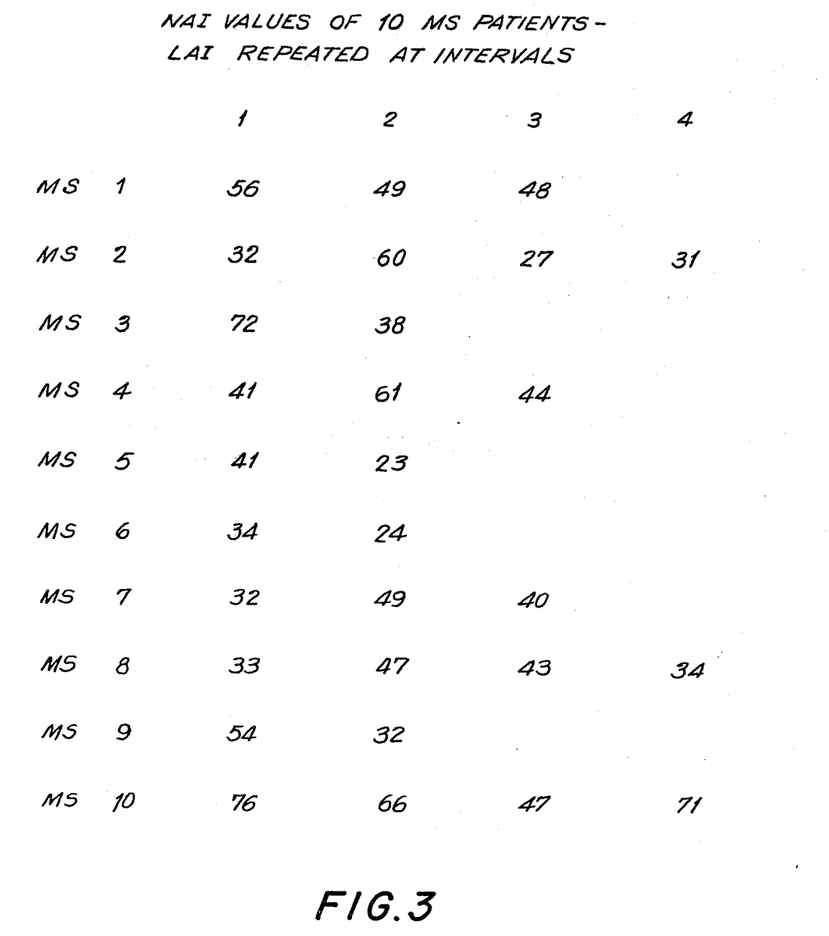
FIG. 3 is a table setting forth the non-adherence index values obtained through periodic application of the methodology of our invention to a group of ten multiple sclerosis patients.

Expression as above of the LAI in terms of the NAI dictated statistical analysis of the NAI values, with the Kolmogorov-Smirnov test, as described in the article entitled "The Lillifors Test" by W. J. Conover at page 302 of *Practical Nonparametric Statistics* published in 1971 by John Wiley & Sons, Inc., New York, N.Y., establishing that the NAI values for both the test and control groups are normally distributed. The mean and standard deviations for the NAI values of FIG. 1 are tabulated in the table of FIG. 2, and are believed to clearly indicate that the NAI values for the MS patients are larger than those for the non-MS subjects, with application of the Mann-Whitney test to these data establishing a probability of less than $10^{-10}$ that the respective data from the test and control groups were obtained from the same population. The results of retesting as above of ten MS patients at different intervals are presented in the table of FIG. 3 and are believed to clearly establish consistency of test results.

(2) Positive diagnosis of MS through use of a latex or microsphere procedure in accordance with the teachings of our invention is accomplished as follows:

Blood Sample Preparation:

Three ml of venous blood is withdrawn from the patient in question into a Sodium Citrate Vacutainer (Becton Dickinson Company, Rutherford, New Jersey) to prevent clotting, and mixed gently by inversion.

Test And Control Extract Preparation:

These preparations are effected in the same manner described in detail hereinabove with regard to utilization of the leukocyte adherence inhibition procedure.

Test And Control Sample Preparation:

0.01 ml of loosely packed latex beads or like leukocyte agglutination means of approximately 7 microns in diameter in a 1% NaCl solution is added to each one of three polystyrene tubes (16×100 ml), hereinafter referred to as "tube 1," "tube 2," and "tube 3." 0.1 ml of the test extract is added to "tube 1," and 0.1 ml of the control extract is added to "tube 2." No extract is added to "tube 3" which is to be used as a procedure control, for detection of bead clumping, only. Sufficient Medium 199 is added to each of the tubes to achieve final tube contents volumes of 0.31 ml. All tubes are then incubated at 37° C. for 45 minutes and gently agitated every 15 minutes to insure thorough mixing; whereupon each of the tubes is centrifuged at 200×g for 5 minutes at 25° C. to complete the coating of the latex beads by the test and control extracts in "tube 1" and "tube 2," respectively. The resultant supernate is discarded from each of the tubes and the resultant pellets are resuspended in the tubes in 0.1 ml of Medium 199 in each instance. One ml of venous blood sample prepared as above is then added to each of the tubes, and the resultant solutions mixed to initiate the preparation of the best sample in "tube 1," the preparation of the control sample in "tube 2," and the preparation of a clumping control sample in "tube 3." 4 to 6 drops of the test sample, the control sample and the clumping control sample are then respectively thinly spread on different ones of three conventional, pre-cleaned microscope slides, hereinafter referred to as the "procedure control slides" which are air-dried and appropriately stained. Each of the tubes is then incubated for two hours at 37° C. to complete the test and control extract-blood sample reactions, if any; whereupon 4 to 6 drops of the test sample, the control sample and the clumping control sample are then respectively thinly spread on different ones of three conventional, pre-cleaned microscope slides, hereinafter referred to as "slide 1," "slide 2," and "slide 3" which are air dried and appropriately stained. Preferably, duplicates of these slides are prepared at the outset for use during testing if and as required.

Test And Control Sample Assay:

Initially, the three "procedure control slides" are examined microscopically at, for example, 10×45 power, and an agglutination index calculated as described hereinbelow. If this agglutination index is greater than 30, the procedure is discarded. Thereafter, "slide 3" is microscopically examined as above to determine if clumping of the latex beads and blood sample leukocytes has occurred to indicate insufficient latex bead-solution mixing and require re-preparation of the test and control samples. In the absence of either of the above, "slides 1" and "2" are examined microscopically at, for example, 10×45 power, with, for example, 1000 cells being counted in each instance. Counting results are divided into two categories in each instance, with any latex bead having 3 or more leukocytes adhering thereto being counted as positive, and any latex bead having 2 or less leukocytes adhering thereto being counted as negative; it being readily understood by those skilled in this art that the tendency of the blood sample leukocytes to clump and adhere to the extract-coated latex beads will be increased in accordance with the extent to which those leukocytes have been sensitized by multiple sclerosis. Cell counting may conveniently be effected through use of automatic visual imaging means taking, for example, the form of the Cyto-Tally or similar scanning cell counter. If desired, cell counting may be conducted in duplicate, using the duplicate slides 1 and 2, and an average calculated. The latex procedure assay results are expressed in terms of a rosetting or agglutination index (hereinafter "AI") in accordance with the following equation:

$$AI = (A-B)/B \qquad \text{Equation 2}$$

wherein:

A is the average number of positive latex beads from slide 1, and B is the average number of positive latex beads from slide 2.

In accordance with the latex procedure, an AI value of greater than 30 has been selected as positive indicia of MS in the patient in question.

(3) Positive diagnosis of MS through use of a radio immunoassay or micro-LAI procedure in accordance with the teachings of our invention is accomplished as follows: it being noted that this procedure is best operable on the lymphocytes, rather than the leukocytes in general, of the blood sample of the patient in question:

Blood Sample Preparation:

Six ml of Hanks Balanced Salt Solution (HBSS) is added to 7 ml of heparinized venous blood from the patient in question and mixed thoroughly by gentle agitation, with the resultant solution being divided into two equal parts. The two solution parts are then respectively carefully layered on two 5 ml polystyrene tubes each containing 3 ml of Lymphocyte Separation Medium (LSM), and then centrifuged at 700×6 for 35 minutes at 25° C. The lymphocytes which separate at the respective tube interfaces during centrifugation are carefully removed with a disposable plastic syringe and long cannula, whereupon the resultant lymphocyte serum suspensions are transferred to and combined in a plastic centrifuge tube, to which is added 3 ml of HBSS, and centrifuged at 200× g for 10 minutes at 25° C. Centrifugation as last described in repeated two additional times, with the supernate being discarded in each instance and the pellet re-suspended in 3 ml of HBSS. The lymphocyte pellet resulting from final centrifugation is then resuspended in 0.5 ml of Medium 199 containing 10% fetal calf serum to adjust the lymphocyte concentration to $1 \times 10^7$, and 0.2 ml sodium chromate 51

(1 mC/ml) as marketed by New England Nuclear, Boston, Mass., added thereto for cell labeling. The solution is then incubated at 37° C. for 45 minutes while being gently agitated on a serological shaker for obvious purpose.

Test And Control Extract Preparation:

These preparations are effected in the same manner described in detail hereinabove with regard to utilization of the leukocyte adherence inhibition procedure.

Test And Control Sample Preparation:

Medium 199 with Hepes to which has been added 10% fetal calf serum (hereinafter "Medium"), the test and control extracts, diluted to protein concentrations of approximately 5 mg/ml (1:30 dilution) with Medium 199, and/or the labeled blood sample cells, are respectively disposed in the 96 wells of a plastic microplate, which contains 8 panels (hereinafter "panels 1 through 8") of 12 wells each, as follows:

51 ul (microliters) of Medium and 1 ul of labeled cells in each of the 12 wells of panel 1;
50 ul of Medium plus 1 ul of labeled cells and 1 ul of test extract in each of the 12 wells of panel 2;
49 ul of Medium plus 1 ul of labeled cells and 2 ul of test extract in each of the 12 wells of panel 3;
48 ul of Medium plus 1 ul of labeled cells and 3 ul of test extract in each well of panel 4;
51 ul of Medium plus 1 ul of test extract in each well of panel 5 for function as a procedure control panel;
50 ul of Medium plus 1 ul of labeled cells and 1 ul of control extract in each well of panel 6;
49 ul of Medium plus 1 ul of labeled cells and 2 ul of control extract in each well of panel 7; and
48 ul of Medium plus 1 ul of labeled cells and 3 ul of control extract in panel 8.

Following the above, the plastic microplate is incubated for 120 minutes at 37° C. to complete the test and control extract-labeled cells reactions, if any. After incubation, the plate is turned over on a paper towel and allowed to drain at room temperature for 20 minutes to enable the reacted, and thus non-adherent, labeled cells to flow out of the panel wells, whereupon the plate is again placed upright and sprayed with a cell exfoliate spray fixator to fix the adherent, labeled cells in the respective wells.

Test And Control Sample Assay:

For assay, the plastic microplate is cut into individual wells which are dropped in turn into a plastic counting tube for counting of the adherent, labeled cells in each of the wells by an Abbott gamma counter as manufactured by Abbott Laboratories of Chicago, Ill. The assay results are expressed in terms of the lymphocyte adherence index (LYAI) in accordance with the following equation:

$$LYAI = \frac{(A - B)}{B} \times 100 \qquad \text{Equation 3}$$

wherein:
A is the mean number of gamma counts per minute for all test wells initially containing the test extract and labeled cells, and B is the mean number of gamma counts per minute for all control wells initially containing the control extract and labeled cells.

A value of greater than 30 for the LYAI from Equation 3 has been selected as positive indicia of MS on the part of the patient in question.

(4) Positive diagnosis of MS through use of a lysis procedure in accordance with the teachings of our invention is accomplished as follows:

Blood Sample Preparation:

Seven ml of venous blood is withdrawn from the patient in question into a plastic disposable syringe to which has been pre-added 2000 units of heparin. This syringe is then secured in an inverted, vertical position and allowed to stand for 1 hour at 25° C., whereupon the same is incubated in a similar position at 37° C. for 30 minutes. The leukocyte-rich plasma is withdrawn and centrifuged in a conical polystyrene tube at 200×g for 5 minutes, whereupon the supernate is discarded and the pellet resuspended in 1 ml of tris-buffered ammonium chloride solution and refrigerated at 4° C. for 15 minutes to lyse the red cells. 5 ml of Medium 199 with Hepes is then added to the tube and the same again centrifuged at 200×g for an additional 5 minutes, whereupon the supernate is again discarded and sufficient Medium 199 with Hepes (approximately 1.2 ml) added to the pellet to resuspend the same with a concentration of approximately $1 \times 10^7$ cells per ml. As an alternative method of blood sample preparation from whole blood, 0.8 ml of venous blood from the patient in question is heparinized and mixed with 5 drops of lyzerglobin to lyse the red blood cells and eliminate the cell separation steps as described hereinabove.

Test And Control Extract Preparation:

These preparations are effected in the same manner described in detail hereinabove with regard to utilization of the leukocyte adherence inhibition procedure.

Test And Control Sample Preparation:

The respective test and control extracts are diluted to protein concentrations of approximately 5 mg/ml (1:30 dilution) with Medium 199. Three pairs of polystyrene tubes (16×100 mm) are then prepared in the following manner: 0.2 ml of the test extract and 0.4 ml of the blood sample cell suspension is added to each of the first tube pair; 0.2 ml of the control extract and 0.4 ml of the blood sample cell suspension is added to each of the second tube pair; while 0.4 ml of the blood sample cell suspension is added to the third tube pair for use as a procedure control; it being understood that the extent to which the blood sample leukocytes are broken up, or lysed, in the first and second tube pairs will be proportional in each instance to the extent of the relevant extract-blood sample leukocyte reaction. Thereafter, sufficient Medium 199 is added to each of the tubes to provide final tube solution volumes of 1 ml.

Test And Control Sample Assay:

0.1 ml of the test and control sample, and 0.1 ml of the diluted blood sample cell suspension are each added to respective 20 ml quantities of isotonic ayide-free cell counting solution (Diluid or Isoton) in plastic cuvettes, and the leukocytes which have not been lysed counted through use of a Coulter D-2 electronic cell counter to provide an initial count. The tubes are then incubated at 37° C. for one hour with gentle shaking every 15 minutes, whereupon leukocyte counting is again accomplished as described to provide a middle count for procedure control purposes. The tubes are then reincubated for one hour at 37° C. with gentle shaking as above, whereupon leukocyte counting as described is accomplished for a third and final time to provide a final count. The percentage of lysis for each tube pair is then calculated in accordance with the following equation:

$$\text{Lysis \%} = 100 \frac{\text{final count}}{\text{initial count}} \quad \text{Equation 4}$$

The lysis index (LI) is then calculated in accordance with the following equation:

$$LI = \frac{\text{Lysis \% (First Tube Pair)} - \text{Lysis \% (Second Tube Pair)}}{\text{Lysis \% (Second Tube Pair)}} \times 100 \quad \text{Equation 5}$$

In accordance with the lysis procedure, an LI value of greater than 20 has been selected as positive indicia of MS in the patient in question.

Preparation of the respective test and control extracts for the immunodiagnosis of malignant diseases of interest is effected in the same general manner as that described hereinabove with regard to the preparation of the test and control extracts for the immunodiagnosis of MS. More specifically, and taking, for example, test and control extract preparation with regard to breast cancer, it may be understood that the test extract would be prepared as described, but from the pooled bloods of a group of at least five donors known to have breast cancer through extraction as described of the breast cancer-related material therefrom; while the control extract would again be prepared as described, but from the pooled bloods of a group of at least five donors known not to have breast cancer. The diagnostic procedures would, in all other respects, remain the same as described hereinabove for the diagnosis of MS.

Figure 4:
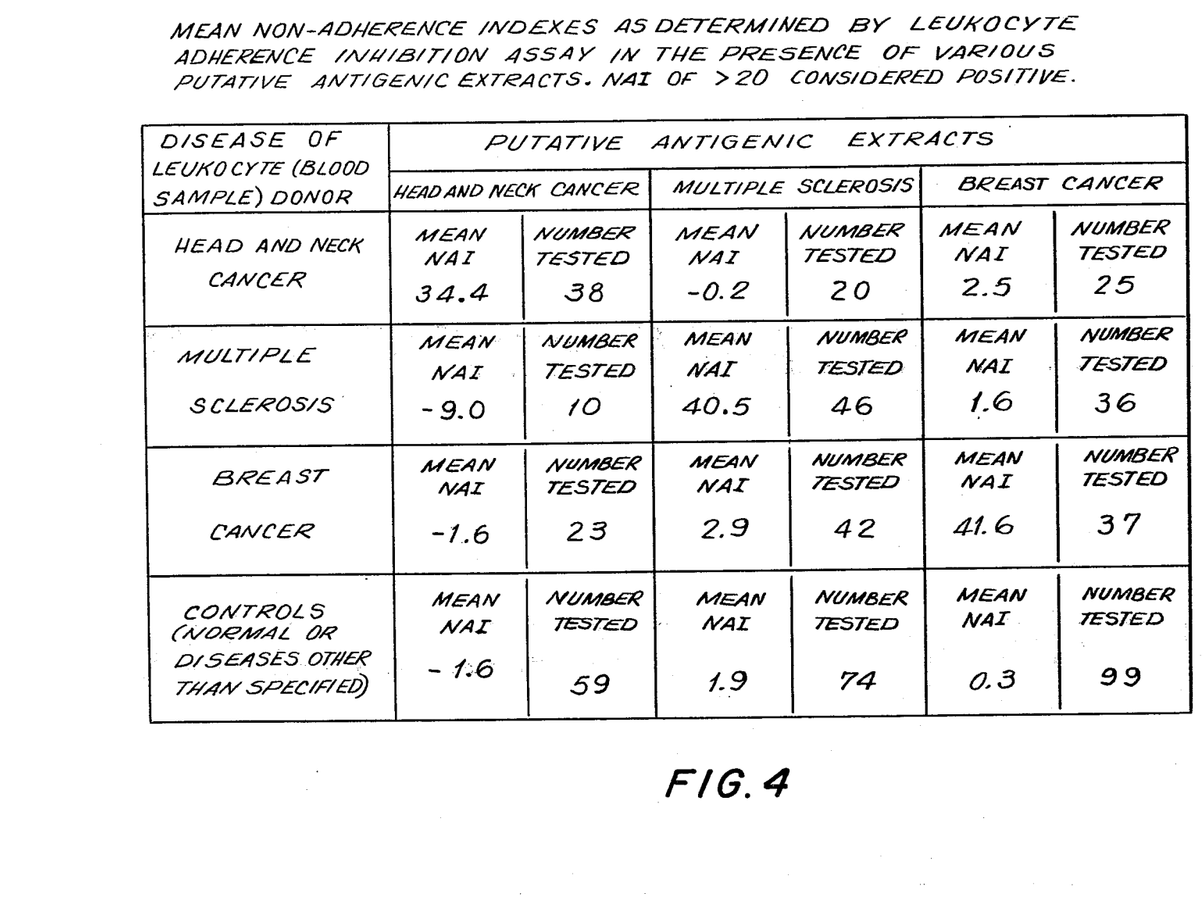
FIG. 4 is a table setting forth the results of validation testing of the specificity fo the putative antigenic extracts of our invention.

Validation of the remarkable specificity of the reactions of the respective test extracts to only the sensitized leukocytes from the blood samples of patients having the same particular disease as that borne by the donors of the pooled bloods from which the test extract in question was prepared, was accomplished by the testing of three different putative antigenic extracts against the sensitized leukocytes from the bloods of MS patients, patients with malignant diseases in the nature of breast cancer, and cancer of the head and neck, respectively, and against the non-sensitized leukocytes of "normal" control patients. The results of this validation testing are presented in the table of FIG. 4, wherein the listed mean NAI values are believed to make clear that the sensitized leukocytes from the blood samples of patients having MS, breast cancer, and head and neck cancer, respectively, are significantly more reactive to the putative antigenic extracts prepared from the blood samples of donors having those same diseases than to the putative antigenic extracts prepared from the blood samples of donors having other and different of the specified diseases. In like manner, FIG. 4 is believed to make clear that non-sensitized leukocytes from the blood samples of normal control donors display a marked non-specificity to all of the putative antigenic extracts in question. In addition, the respective NAI values of FIG. 5 are believed to indicate the absence of significant cross-reactivity between the respective putative antigenic extracts of interest.

Advantageously, we have extended the teachings of our invention by the discovery that the respective test and control extracts may be effectively prepared from body substances other and different from blood which have also been found to contain the MS-related materials and the malignant disease-related materials of interest; it being understood by those skilled in this art that certain other body substances, as specified hereinbelow, may be more readily available in the necessary quantities to thus facilitate the relatively large scale advance preparation of the extracts. More specifically, and for MS diagnosis, it has been further discovered that the respective test and control extracts may alternatively be respectively prepared from body substances taking the form of the appropriately concentrated, pooled urines of a plurality (again, for example, five) donors known to have MS in accordance with the Rose et al. diagnostic criteria specified hereinabove; and from the appropriately concentrated pooled urines of a like plurality of donors known not to have MS in accordance with those same diagnostic criteria. Under these circumstances, it may be understood that test and control extract preparation would be effected in the manner described in detail hereinabove excepting for the fact that the same would commence, in each instance, with body substances taking the form of the pooled, appropriately concentrated urines, rather than the pooled bloods, of the known MS, and known non-MS, donors. Blood sample preparation, test and control sample preparation, and test and control sample assay would, in each instance, and with regard to each procedure, remain as described.

In like manner, and for diagnosis of malignant disease in the nature, for example, of breast cancer, or cancer of the head and neck, it has further been discovered that test and control extract preparation may alternatively be respectively effected from the pooled pleural fluids, ascites fluids, supernates of tumor cells, tumor cells grown in culture media, or concentrated urines, or like substances, of a plurality (again, for example, five) donors known to have the specific type of cancer of interest in accordance with traditional diagnostic techniques; and from the pooled pleural fluids, ascites fluids, supernates of tumor cells, tumor cells grown in culture media or concentrated urines of a like plurality of donors known not to have the specific type of cancer of interest in accordance with those same diagnostic techniques. Again, blood sample preparation, and test and control sample preparation and assay would, in each instance, and with regard to each procedure, remain as described.

By all of the above is believed made clear that the diagnosis of MS or malignant disease may be readily and positively effected in accordance with the teachings of our invention as described through the simple withdrawal of a blood sample from the patient in question, and without regard for the particular body substance, that is blood, urine, pleural fluid, ascites fluid, supernates of tumor cells, or tumor cells grown in culture media, or like substance, from which the respective test and control extracts were prepared.

Various changes may, of course, be made in the methodology of our invention as disclosed herein without departing from the spirit and scope of our invention as defined in the appended claims.

We claim:

1. A method for the diagnosis of multiple sclerosis by blood sample analysis which comprises the steps of mixing a putative antigenic blood extract prepared from multiple sclerosis-sensitized blood and specific to multiple sclerosis-sensitized blood leukocytes with leukocytes of the blood sample and promoting the reaction therebetween to inhibit the ability of the multiple sclerosis-sensitized leukocytes of the blood sample to adhere to a glass surface, and determining the extent to which said leukocyte adherence ability has been inhibited.

2. The method of claim 1 further comprising the step of separating out the leukocytes of said blood sample prior to mixing with said blood extract.

3. The method of claim 1 further comprising the step of pooling the whole bloods of a plurality of donors known to have multiple sclerosis and preparing said blood extract therefrom for mixing with the leukocytes of said blood sample.

4. A method for the diagnosis of multiple sclerosis by blood sample analysis which comprises the steps of labeling the lymphocytes in the blood sample with an energy-emitting material, mixing a putative antigenic blood extract prepared from multiple sclerosis-sensitized blood and specific to multiple sclerosis-sensitized blood leukocytes with the lymphocytes of the blood sample and promoting the reaction therebetween to inhibit the ability of the multiple sclerosis-sensitized lymphocytes of the blood sample to adhere to a glass surface, and determining by energy-emitting material detection the extent to which said lymphocyte adherence ability has been inhibited.

5. The method of claim 4 further comprising the step of separating out the lymphocytes of said blood sample prior to mixing with said blood extract.

6. The method of claim 4 further comprising the step of pooling the whole bloods of a plurality of donors known to have multiple sclerosis and preparing said blood extract therefrom for mixing with the lymphocytes of said blood sample.

7. The method of claim 4 further comprising the step of labeling the lymphocytes of said blood sample with a radioactive material.

8. A method for the diagnosis of multiple sclerosis by blood sample analysis which comprises the steps of coating agglutination means with a putative antigenic blood extract prepared from multiple sclerosis-sensitized blood and specific to multiple sclerosis-sensitized blood leukocytes to enhance the capability of said agglutination means to cause clumping of multiple sclerosis-sensitized blood leukocytes, contacting the thusly coated agglutination means with the leukocytes of said blood sample and promoting the reaction therebetween to cause clumping of the multiple sclerosis-sensitized leukocytes of the blood sample and determing the extent to which said blood sample leukocytes have clumped.

9. The method of claim 8 further comprising the step of separating out the leukocytes of said blood sample prior to contacting thereof with said agglutination means.

10. The method of claim 8 further comprising the step of pooling the whole bloods of a plurality of donors known to have multiple sclerosis and preparing said blood extract therefrom for coating said agglutination means.

11. A method for the diagnosis of multiple sclerosis by blood sample analysis which comprises the steps of mixing a putative antigenic blood extract prepared from multiple sclerosis-sensitized blood and specific to multiple sclerosis-sensitized blood leukocytes with the leukocytes of the blood sample and promoting the the reaction therebetween to lyse the multiple sclerosis-sensitized leukocytes of the blood sample and determining the extent to which the blood sample leukocytes have been lysed.

12. The method of claim 11 further comprising the step of separating out the leukocytes of said blood sample prior to mixing with said blood extract.

13. The method of claim 11 further comprising the step of lysing the red blood cells of said blood sample prior to mixing the leukocytes of said blood sample with said blood extract.

14. The method of claim 11 further comprising the step of pooling the whole bloods of a plurality of donors known to have multiple sclerosis and preparing said blood extract therefrom for mixing with the leukocytes of said blood sample.

15. A method for the preparation of a putative antigenic blood extract specific to multiple sclerosis which comprises the steps of pooling the whole bloods from a plurality of donors known to have multiple sclerosis, placing said pooled whole bloods in solution, concentrating putative antigenic multiple sclerosis-sensitized components present in said pooled whole bloods, separating said concentrated components from said solution, and clarifying said components to form said blood extract.

16. The method of claim 15 wherein the pooled whole bloods placed in solution are mixed with a non-isotonic medium.

17. The method of claim 15 wherein said putative antigenic multiple sclerosis-sensitized components are concentrated and separated from said solution by centrifuging said solution, dialyzing the resultant supernate, centrifuging the resultant non-dialysate and filtering the resultant supernate.

18. The method of claim 15 wherein said putative antigenic multiple sclerosis-sensitized components are clarified by placing the separated and concentrated components in isotonic solution and centrifuging said isotonic solution.

19. A method for the preparation of a putative antigenic blood extract specific to multiple sclerosis which comprises the steps of pooling the whole bloods from a plurality of donors known to have multiple sclerosis, placing said pooled whole bloods in non-isotonic solution, concentrating putative antigenic multiple sclerosis-sensitized components present in said pooled whole bloods, separating said concentrated components from said solution, placing the thusly separated and concentrated putative antigenic multiple sclerosis-sensitized components in isotonic solution and clarifying said components to form said blood extract.

20. A method of claim 19 wherein the whole bloods of at least five donors known to have multiple sclerosis are pooled.

21. A method for the diagnosis of a specific malignant disease of interest by blood sample analysis which comprises the steps of mixing a putative antigenic blood extract prepared from blood sensitized to said malignant disease, said extract being specific to malignant disease-sensitized blood leukocytes, with leukocytes of the blood sample and promoting the reaction therebetween to inhibit the ability of the malignant disease-sensitized leukocytes of the blood sample to adhere to a glass surface and determining the extent to which said leukocyte adherence ability has been inhibited.

22. The method of claim 21 further comprising the step of pooling the whole bloods of a plurality of donors known to have the specific malignant disease of interest and preparing said blood extract therefrom for mixing with the leukocytes of said blood sample.

23. A method for the diagnosis of a specific malignant disease of interest by blood sample analysis which comprises the steps of labeling the lymphocytes in the blood sample with an energy-emitting material, mixing a putative antigenic blood extract prepared from blood sensitized to said malignant disease said extract being specific to malignant disease-sensitized blood leukocytes with the lymphocytes of said blood sample and promoting the reaction therebetween to inhibit the ability of the blood sample to adhere to a glass surface and determining by energy-emitting material detection the extent to which said lymphocyte adherence ability has been inhibited.

24. The method of claim 23 further comprising the step of pooling the whole bloods of a plurality of donors known to have the specific malignant disease of interest and preparing said blood extract therefrom for mixing with the lymphocytes of said blood extract.

25. A method for the diagnosis of a specific malignant disease of interest by blood sample analysis which comprises the steps of coating agglutination means with a putative antigenic blood extract prepared from blood sensitized to said malignant disease, said extract being specific to malignant disease-sensitized blood leukocytes, to enhance the capability of said agglutination means to cause clumping of malignant disease-sensitized blood leukocytes, contacting the thusly coated agglutination means with the leukocytes of said blood sample and promoting the reaction therebetween to cause clumping of the malignant disease-sensitized leukocytes of the blood sample and determining the extent to which said blood sample leukocytes have clumped.

26. The method of claim 25 further comprising the step of pooling the whole bloods of a plurality of donors known to have the malignant disease of interest and preparing said blood extract therefrom for coating of said agglutination means.

27. A method for the diagnosis of a specific malignant disease of interest by blood sample analysis which comprises the steps of mixing a putative antigenic blood extract prepared from blood sensitized to said malignant disease, said extract being specific to malignant disease-sensitized blood leukocytes, with the leukocytes of said blood sample and promoting the reaction therebetween to lyse the malignant disease-sensitized leukocytes of the blood sample and determining the extent to which the blood sample leukocytes have been lysed.

28. The method of claim 27 further comprising the step of pooling the whole bloods of a plurality of donors known to have the malignant disease of interest and preparing said blood extract therefrom for mixing with the leukocytes of said blood sample.

29. A method for the preparation of a putative antigenic blood extract specific to a particular malignant disease of interest which comprises the steps of pooling the whole bloods from a plurality of donors known to have the malignant disease of interest, placing said pooled whole bloods in solution, concentrating putative antigenic malignant disease-sensitized components present in said pooled whole bloods, separating said concentrated components from said solution, and clarifying said components to form said blood extract.

30. A method for the preparation of a putative antigenic blood extract specific to a particular malignant disease of interest which comprises the steps of pooling the whole bloods from a plurality of donors known to have the malignant disease of interest, placing said pooled whole bloods in non-isotonic solution, concentrating the putative antigenic malignant disease-sensitized components present in said pooled whole bloods, separating said concentrated components from said solution, placing the thusly separated and concentrated putative antigenic malignant disease-sensitized components in isotonic solution, and clarifying said components to form said blood extract.

31. A method for the diagnosis of multiple sclerosis by blood sample analysis which comprises the steps of mixing a putative antigenic blood extract prepared from multiple sclerosis-sensitized blood and specific to multiple sclerosis-sensitized blood leukocytes with leukocytes of said blood sample and promoting the reaction therebetween to detect the presence of multiple sclerosis-sensitized leukocytes in the blood sample, and quantifying the amount of multiple sclerosis disease-sensitized blood leukocytes.

32. The method of claim 31 further comprising the step of pooling the whole bloods from a plurality of donors known to have multiple sclerosis and preparing said blood extract therefrom for mixing with the leukocytes of said blood sample.

33. A method for the diagnosis of a specific malignant disease of interest by blood sample analysis which comprises the steps of mixing a putative antigenic blood extract prepared from blood sensitized to said malignant disease, said extract being specific to malignant disease-sensitized blood leukocytes, with leukocytes of said blood sample and promoting the reaction therebetween to detect the presence of malignant disease-sensitized leukocytes in the blood sample, and quantifying the amount of malignant disease-sensitized blood leukocytes.

34. The method of claim 33 further comprising the step of pooling the whole bloods from a plurality of donors known to have the specific malignant disease of interest and preparing said blood extract therefrom for mixing with the leukocytes of said blood sample.

35. A method for the diagnosis of multiple sclerosis by blood sample analysis which comprises the steps of mixing a putative antigenic urine extract prepared from multiple sclerosis-sensitized urine and specific to multiple sclerosis-sensitized blood leukocytes with leukocytes of said blood sample and promoting the reaction therebetween to detect the presence of multiple sclerosis-sensitized leukocytes in the blood sample, and quantifying the amount of multiple sclerosis disease-sensitized blood leukocytes.

36. A method of claim 35 further comprising the step of pooling the urine from a plurality of donors known to have multiple sclerosis and preparing said urine extract therefrom for mixing with the leukocytes of said blood sample.

37. A method for the diagnosis of a specific malignant disease of interest by blood sample analysis which comprises the steps of mixing a putative antigenic body substance extract prepared from body substance sensitized to said from malignant disease, said extract being specific to malignant disease-sensitized blood leukocytes, with leukocytes of said blood sample and promoting the reaction therebetween to detect the presence of malignant disease-sensitized leukocytes in the blood sample, and quantifying the amount of malignant disease-sensitized blood leukocytes.

38. The method of claim 37 further comprising the step of pooling the body substance of a plurality of donors known to have the malignant disease of interest and preparing said body substance extract therefrom for mixing with the leukocytes of said blood sample.

39. The method of claim 37 further comprising the step of pooling the pleural fluids of a plurality of donors known to have the malignant disease of interest and preparing said pleural extract therefrom for mixing with the leukocytes of said blood sample.

40. The method of claim 37 further comprising the step of pooling the ascites fluids of a plurality of donors known to have the malignant disease of interest and preparing said ascite extract therefrom for mixing with the leukocytes of said blood sample.

41. The method of claim 37 further comprising the step of pooling the supernates of tumor cell cultures of a plurality of donors known to have the specific malignant disease of interest and extracting said tumor cell extract therefrom for mixing with the leukocytes of said blood sample.

42. The method of claim 37 further comprising the step of pooling tumor cells grown in culture media from a plurality of donors known to have the specific malignant disease of interest and preparing said tumor cell extract therefrom for mixing with the leukocytes of said blood sample.

43. A method for the preparation of a putative antigenic urine extract specific to multiple sclerosis which comprises the steps of pooling the urines of a plurality of donors known to have multiple sclerosis, placing said pooled urines in solution, concentrating putative antigenic multiple sclerosis-sensitized components present in said pooled urines, separating said concentrated components from said solution, and clarifying said components to form said urine extract.

44. The method of claim 43 wherein said pooled urines in solution are mixed with a non-isotonic medium.

45. A method for the preparation of a putative antigenic urine extract specific to a particular malignant disease of interest which comprises the steps of pooling the urines from a plurality of donors known to have the malignant disease of interest, placing said pooled urines in solution, concentrating putative antigenic malignant disease-sensitized components present in said pooled urine, separating said concentrated components from said solution, and clarifying said components to form said urine extract.

46. The method of claim 45 wherein said pooled urines in solution are mixed with a non-isotonic medium.

47. A method for the preparation of a putative antigenic pleural extract specific to a malignant disease of interest which comprises the steps of pooling the pleural fluids of a plurality of donors known to have the malignant disease of interest, placing said pooled pleural fluids in solution, concentrating putative antigenic malignant disease-sensitized components present in said pooled pleural fluids, separating said concentrated components from said solution, and clarifying said components to form said pleural extract.

48. A method for the preparation of a putative antigenic ascite extract specific to a malignant disease of interest which comprises the steps of pooling the ascite extract of a plurality of donors known to have the malignant disease of interest, placing said pooled ascite extract in solution, concentrating putative antigenic malignant disease-sensitized components present in said pooled ascites, separating said concentrated components from said solution, and clarifying said components to form said ascite extract.

49. A method for the preparation of a putative antigenic tumor cell extract specific to a malignant disease of interest which comprises the steps of pooling the supernates of tumor cell cultures of a plurality of donors known to have the malignant disease of interest, placing said pooled supernates of tumor cell cultures in solution, concentrating putative antigenic malignant disease-sensitized components present in said pooled supernates, separating said concentrated components from said solution, and clarifying said components to form said tumor cell extract.

50. A method for the preparation of a putative antigenic tumor cell extract specific to a malignant disease of interest which comprises the steps of pooling tumor cell grown in culture media from a plurality of donors known to have the malignant disease of interest, placing said pooled tumor cells grown in culture media in solution, concentrating putative antigenic malignant disease-sensitized components present in said pooled tumor cells, separating said concentrated components from said solution, and clarifying said components to form said tumor cell extract.

* * * * *